(12) United States Patent
Rethmeier et al.

(10) Patent No.: US 9,603,541 B2
(45) Date of Patent: Mar. 28, 2017

(54) BIO-MEDICAL ELECTRODE

(71) Applicant: KONINKLIJKE PHILIPS N.V., Eindhoven (NL)

(72) Inventors: Karel Frederik Rethmeier, Eindhoven (NL); Severin Luc Ramses Harvey, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/432,916

(22) PCT Filed: Sep. 3, 2014

(86) PCT No.: PCT/EP2014/068641
§ 371 (c)(1),
(2) Date: Apr. 1, 2015

(87) PCT Pub. No.: WO2015/036288
PCT Pub. Date: Mar. 19, 2015

(65) Prior Publication Data
US 2016/0183831 A1    Jun. 30, 2016

(30) Foreign Application Priority Data
Sep. 16, 2013 (EP) .................................. 13184567

(51) Int. Cl.
*A61B 5/0408* (2006.01)
*A61N 1/04* (2006.01)
(Continued)

(52) U.S. Cl.
CPC .......... *A61B 5/0416* (2013.01); *A61B 5/0478* (2013.01); *A61B 5/0492* (2013.01);
(Continued)

(58) Field of Classification Search
CPC ... A61B 5/0416; A61B 5/0478; A61B 5/0492; A61B 2562/0209; A61B 2562/227; A61N 1/0452; A61N 1/0456; A61N 1/048
(Continued)

(56) References Cited

U.S. PATENT DOCUMENTS 441,501 A    11/1890   Mandleberg et al.
3,841,312 A * 10/1974  Corasanti ............. A61B 5/0416
                                                600/391
(Continued)

FOREIGN PATENT DOCUMENTS

CN    103220969 A    7/2013
EP      0390400 A1  10/1990
(Continued)

*Primary Examiner* — Lee S Cohen
*Assistant Examiner* — Erin M Cardinal

(57) ABSTRACT

The invention relates to a bio-medical electrode (100). In a preferred embodiment, an electrode interface comprises a top part (10) with an aperture and a bottom part (20). The bottom part (20) has a head portion designed for a fixation in said aperture and a flexible flange that clamps electrode sheets (31,32) in the connected state of the electrode interface such that the contact force between top and bottom parts is approximately constant during lifetime of the electrode interface. The top part (10) may preferably have the shape of a disk of magnetic or magnetizable material. The bottom part (20) may preferably be made from a conductive plastic such as ABS. The electrode interface may particularly be used in a TENS device.

13 Claims, 3 Drawing Sheets

(51) Int. Cl.
*A61B 5/0416* (2006.01)
*A61B 5/0478* (2006.01)
*A61B 5/0492* (2006.01)

(52) U.S. Cl.
CPC ........... *A61N 1/048* (2013.01); *A61N 1/0452* (2013.01); *A61N 1/0456* (2013.01); *A61B 2562/0209* (2013.01)

(58) Field of Classification Search
USPC ........................................ 600/372, 382, 394
See application file for complete search history.

(56) References Cited

U.S. PATENT DOCUMENTS

| | | | | |
|---|---|---|---|---|
| 4,112,941 A | * | 9/1978 | Larimore | A61B 5/0416 |
| | | | | 439/153 |
| 4,350,165 A | | 9/1982 | Striese | |
| 4,787,390 A | * | 11/1988 | Takata | A61N 1/04 |
| | | | | 600/394 |
| 4,938,219 A | * | 7/1990 | Ishii | A61B 5/0408 |
| | | | | 600/391 |
| 4,996,989 A | | 3/1991 | Stundel et al. | |
| 5,928,142 A | * | 7/1999 | Cartmell | A61B 5/04087 |
| | | | | 600/372 |
| 6,434,410 B1 | * | 8/2002 | Cordero | A61B 5/04085 |
| | | | | 600/391 |
| 2005/0261565 A1 | * | 11/2005 | Lane | A61B 5/0416 |
| | | | | 600/394 |
| 2009/0112283 A1 | | 4/2009 | Kriksunov et al. | |
| 2011/0004090 A1 | * | 1/2011 | Keightley | A61B 5/0408 |
| | | | | 600/383 |
| 2012/0131773 A1 | | 5/2012 | DeGelis et al. | |
| 2013/0023816 A1 | | 1/2013 | Bachinski et al. | |
| 2013/0066412 A1 | | 3/2013 | Van Der Beek et al. | |

FOREIGN PATENT DOCUMENTS

| | | |
|---|---|---|
| EP | 0884021 A1 | 12/1998 |
| WO | 7900042 A1 | 2/1979 |
| WO | 2012001643 A1 | 1/2012 |

* cited by examiner

BIO-MEDICAL ELECTRODE

CROSS-REFERENCE TO PRIOR APPLICATIONS

This application is the U.S. National Phase application under 35 U.S.C. §371 of International Application No. PCT/EP2014/068641, filed on Sep. 3, 2014, which claims the benefit of European Patent Application No. EP 13184567.9, filed on Sep. 16, 2013. These applications are hereby incorporated by reference herein.

FIELD OF THE INVENTION

The invention relates to a bio-medical electrode for a bio-medical device.

BACKGROUND OF THE INVENTION

Electrodes are used in biomedical applications, such as neuromuscular stimulation. Further, these electrodes are typically connected with snap fixation or a cable connector. Typical snap fixation involves two parts; a top protruding head that fits into a device directly and a bottom part, which is also protruded, that also fits into the top part. Electrode sheets are typically fixed/arranged in between the top part and bottom part. There are multiple disadvantages to such an assembly.

Firstly, due to nature of snap fixation the forces while affixing the electrode to the device cannot be controlled. For instance, a user may apply larger force while connecting or disconnecting the electrode to and from the device. In such instances, the snap connector assembly (i.e. the two parts) typically damages the electrode sheets there between thereby decreasing the lifetime of the electrode. Secondly, by the nature of design of the two parts, the relative height of the connector, including the top part and the bottom part, is also high, which in many instances may be undesirable. Thirdly, the current snap connectors do not offer consistent electrical conductance between the device and the electrode, especially when the user is mobile. In this instance the user movement transmitted to the snap fixation can cause the electrode sheets to lose contact with the top or bottom part and thereby loss of electrical contact with the skin. One such snap connector assembly is also described in EP0390400A1.

SUMMARY OF THE INVENTION

It would be advantageous to have a bio-medical electrode for a fast and reliable connection with an associated bio-medical device.

This object is addressed by a bio-medical electrode, herein after referred to as the electrode, according to claim 1. Preferred embodiments are disclosed in the dependent claims. Various examples of electrodes include but are not limited to at least one of a TENS electrode, an ECG electrode, a EEG electrode, an electromyography electrode, an electrical muscle stimulation electrode, a neuromuscular stimulation electrode, and a functional electrical stimulation electrode.

An electrode construction according to an embodiment of the invention serves for connecting material of an electrode, i.e. the electrode sheets, for example a flexible conductive sheet of an electrode for biomedical applications, to some external controller (for instance, a TENS device) and/or to a line leading to such a controller. The electrode comprises the following components:

a) a flat top part having an aperture;
b) a bottom part having:
   a flexible flange having an upward inclination;
   an upward projecting head portion that can be fixed in the aperture, the upward projecting head disposed on the flexible flange;
   a flange disposed at the transition between the head portion and flexible flange; and
c) an electrode material;
wherein, the flange is arranged to provide a stop to create a pre-defined deflection of the flexible flange when the flat top part along with the electrode material is pressed against the flexible flange.

In the above definition of the electrode, spatial attributes such as "top", "bottom", and "upward" refer to a particular reference orientation of the electrode in its assembled state. This reference orientation is only used to better explain the mutual positioning of components. It is in no way limiting, and the electrode can of course be used in any spatial orientation that is required by the application at hand.

The top part and the bottom part are usually electrically conductive. The electrical conductivity of the top part and/or of the bottom part preferably matches the conductivity of electrode material clamped between top and bottom part.

The aperture in the top part is preferably an interior aperture, i.e. completely surrounded by material of the top part. Moreover, the aperture is preferably a through-hole extending through the whole thickness of the top part, though it is also compromised by the invention that the aperture is just a recess of limited depth in a surface of the top part.

The aperture will typically have a simple geometric shape, particularly a rotationally symmetric circular shape, though any other regular or irregular shape is possible, too.

The top part and/or the bottom part, also may be referred to as an electrode interface, will typically be a single-piece component. It may be rotationally symmetric about a given axis. Preferably, both the top and the bottom parts are rotationally symmetric about their axis of junction, e.g. an axis along which the bottom part has can be moved to achieve a fixation in the aperture of the top part (in the reference orientation of the electrode interface, this axis is usually vertical). Due to the rotational symmetry, top part and bottom part (electrode interface) will fit together in any relative angular orientation about the axis, which facilitates manufacturing and usage.

The flexibility of the flange implies that it can be moved relative to the rest of the bottom part if it is subjected to a force or pressure. Typically, the flange will be elastic or resilient, i.e. it has a resting position to which it tends back with a force that increases with increasing deflection from said position.

The described electrode along with an electrode material such as a flexible conductive sheet or stack of sheets allows for a reliable attachment by clamping this material between the top part and the flexible flange of the bottom part, wherein a pressure is exerted on the electrode material by the flexible flange. This pressure of the flexible flange guarantees that the electrode material is securely held in place even after a long time of usage during which relaxation and loosening would normally occur in many connections.

In the following, various preferred embodiments of the invention will be described in more detail.

The pressure with which the flexible flange presses against (electrode-) material/contact sheet(s) between the flexible flange and the top part can be adjusted by an appropriate choice of the geometry and/or the material of the flexible flange. Preferably, the flexible flange is designed such that this pressure generates a total force ranging between about 5 N and about 20 N, most preferably between about 10 N and about 15 N. Such forces are large enough to securely fix electrode material without damaging it. Different geometrical shapes and designs are possible for the flexible flange. According to one preferred embodiment, the flexible flange has at least locally an upward inclination, i.e. an inclination towards the top part (in the assembled state of the electrode interface). Preferably, this inclination is such that the associated part of the flexible flange approaches the top part more and more with increasing distance from the head portion. Radially peripheral parts of the flexible flange ("radially" with respect to the head portion as center) will thus be closest to the top part and first contact electrode material when the electrode interface is assembled.

In an embodiment of the invention, each of the distal ends of the upward inclination of the flexible flange is at a first pre-determined height from the base of the flexible flange. Further, another flange (stop element) is at a second pre-determined height from the base of the flexible flange. In various embodiments of the invention, the first pre-determined height is greater than the second pre-determined height. Furthermore, during assembly, the top part is pressed against the flexible flange and is encountered by the flange (stop element). Due to this stop, under the influence of the downward force, the flexible flange goes under a deflection. In other words, each of the distal ends of the flexible flange moves from the first pre-determined height to the second pre-determined height.

In the aforementioned embodiment, there may be one or a few separate portions of the flexible flange having the upward inclination. In a preferred embodiment, the flexible flange has the shape of a (usually truncated) cone, providing an upward inclination towards the top part everywhere around the cone axis. Thus a rotational symmetric clamping of electrode material can be achieved.

A preferred and simple geometry that comprises the above features of the bottom part is achieved if a cylindrical head portion (e.g. with a circular cross section) extends upwards while being located in the center of a (upside-down) truncated cone.

In order to provide for a good electrical contact to the electrode material, the bottom part may preferably be electrically conductive.

Additionally or alternatively, the bottom part may comprise a material selected from the group consisting of metal and plastic, particularly an electrically conductive plastic. Preferably, the plastic may contain some filling material, for example carbon, to provide a well-defined degree of electrical conductivity. The plastic may for example comprise acrylonitrile butadiene styrene (ABS).

Additionally or alternatively, the bottom part can optionally be coated with a conductive material to improve the conductivity and/or the electrochemical properties. Typical conductive coatings that can be used are gold (Au), silver (Ag) or silver silver chloride (AgAgCl).

The bottom surface of the top part, which faces the flexible flange of the bottom part in the assembled state of the electrode interface, will typically have a design and geometry that allows for the intended clamping of electrode material. In a preferred and particularly simple embodiment, the top part has a substantially flat bottom surface facing the bottom part (or, more precisely, the flexible flange of the bottom part). A particularly preferred and simple shape of the top part is that of a flat disk (or ring) with a central aperture. The top part could optionally also have holes or gaps in it.

In an embodiment of the invention, the top part is (as a whole or partially) magnetic or magnetizable. This allows for a connection to external equipment, such as a TENS device, by magnetic forces, which is both comfortable and reliable. Further details of such a magnetic connection may be found in the WO 2011/151742 A1, which is incorporated into the present application by reference. In general, the top part may preferably be made from or at least comprise a metal, particularly a magnetic or magnetizable steel.

In another embodiment of the invention, the top part is non-magnetic. In such a case, the electrode connects with the external equipment/device, such as a TENS device, by means of a lead wire. Typically both the electrode and the device include a corresponding male/female connector to electrically and mechanically connect with each other.

Fixation of the head portion of the bottom part in the aperture of the top part may be achieved by any appropriate technology, particularly via a snap connection or a press fit. In this context, the term "press fit" shall as usual denote a situation in which the head portion fits into the aperture with a small oversize such that aperture and head portion exert a pressure onto each other in their assembled state. The dimensions (and materials) of both parts can be chosen such that this pressure is high enough to provide a secure fixation of the bottom part in the top part during normal usage, which can only be overcome by an excess power (which is possibly accompanied by a destruction of top part and/or bottom part). A press fit provides a good mechanical and electrical connection between top and bottom part.

In order to avoid damaging of components of the electrode interface and/or of electrode material, the edges of the aperture in the top part are preferably rounded. Similarly, the edges of the head portion of the bottom part are preferably rounded in order to allow for a smooth attachment of external equipment. The head portion is preferably high enough to extend, in the assembled state of the electrode interface, above the top part.

The aforementioned contact sheet is intended for making electrical contact to the body of a subject in a sufficiently large area. To this end, the sheet is usually made from a flexible material which adapts well to a body contour but can only badly be connected to external equipment. To provide for such a connection, the described electrode interface is used which clamps the conductive sheet in a long-term secure manner while simultaneously providing means for an easy and reliable connection to external equipment.

In general, the above mentioned contact sheet of the electrode may be clamped with just one edge between the flexible flange and the top part of the electrode interface. In a preferred embodiment, the sheet has however a hole through which the head portion of the bottom part extends in the assembled state of the electrode. This provides a positive fit, wherein the sheet may additionally be clamped circumferentially between the top and bottom parts.

BRIEF DESCRIPTION OF THE DRAWINGS

These and other aspects of the invention will be apparent from and elucidated with reference to the embodiments described hereinafter.

In the drawings:

FIG. 5 shows a section through the top and bottom part of the electrode interface in the connected state without an electrode sheet clamped in between.

Like reference numbers refer in the Figures to identical or similar components.

DETAILED DESCRIPTION OF EMBODIMENTS

In the following, an embodiment of the invention will be described with reference to a transcutaneous electrical nerve stimulation (TENS) device. Such a device comprises at least one electrode that is attached to the skin of a person, and its purpose is to conduct electrical pulses from the TENS device into the skin. The coupling in the interface between the electrode and the TENS device may for example be based on a standard wired connection or, preferably, on magnetic forces.

An electrode consists of a multi-layer stack of sheets and an interface to make a mechanical and electrical connection to the electrical system. The electrode used for this purpose consists of three main parts:

An upper flat part.

A multi-layer electrode in between.

A lower plastic part (eyelet). This plastic part can be made of a conductive plastic and be pressed into the flat part. This plastic eyelet shall make good electrical contact to the electrode. To have a well-defined contact force between the electrode material and the plastic part, the plastic part may have a conical flange that acts as a spring during lifetime.

If a magnetic connection is used, the magnetic part, i.e. the upper part, of the electrode interface is flat and thus avoids any gap between the magnet (in the TENS device) and the flat metal part and thereby ensures a constant magnetic force. This is further explained with the help of description of the figures below.

Figure 1:
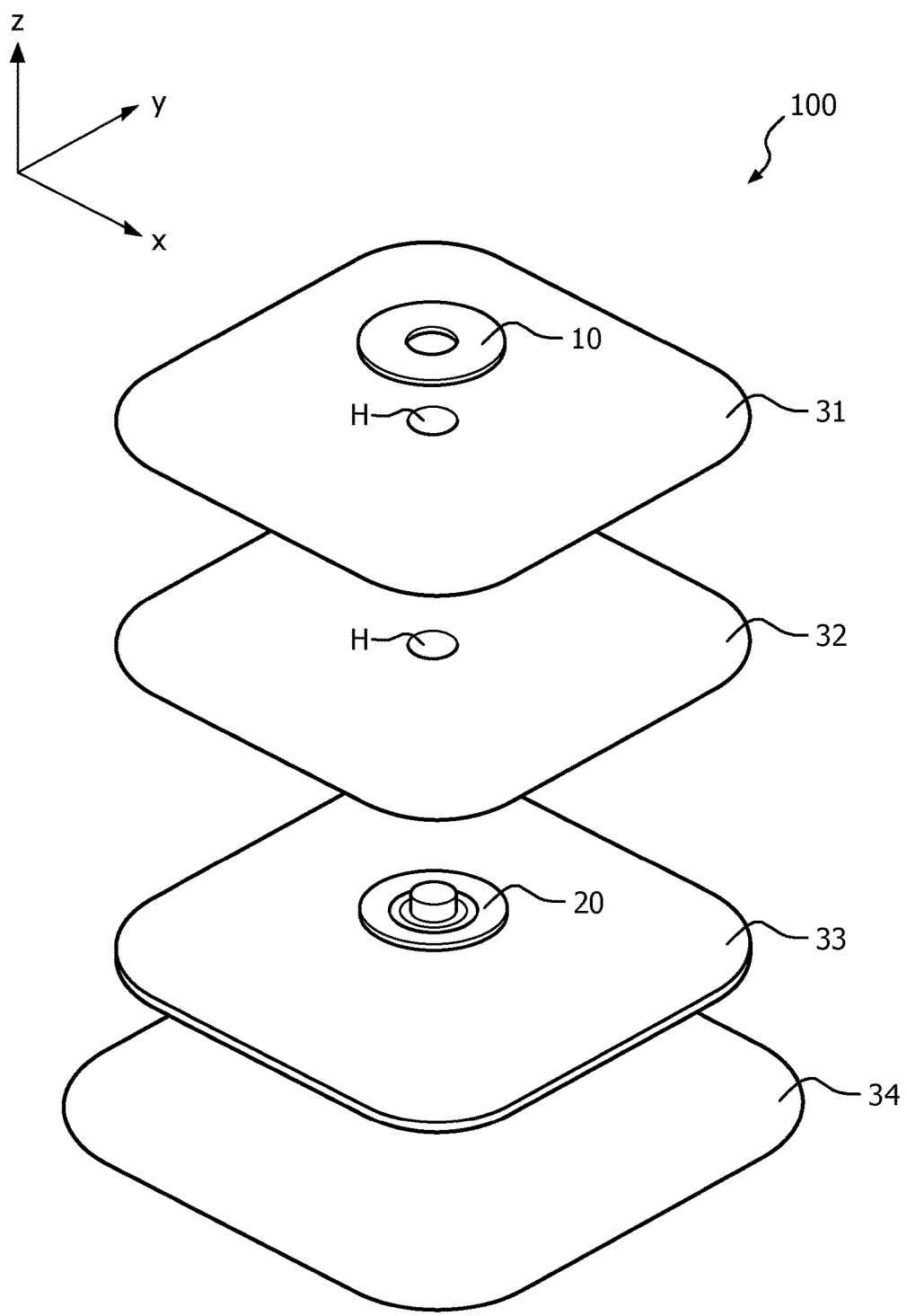
FIG. 1 is an exploded view of an electrode according to an embodiment of the present invention.

FIG. 1 shows in a perspective exploded view a biomedical electrode 100, hereinafter referred to as electrode 100, according to an embodiment of the present invention. It should be noted in this context that the Figures show the electrode and its components in a reference orientation, in which the vertical z-axis corresponds to the direction of assemblage and in which a subject would be placed below the electrode and external connection is made from the top. The electrode 100 comprises the following main components:

Several sheets 31, 32, 33, 34 of electrode material having substantially the same size. The sheets/electrode sheets are stacked to provide different functions. In particular, there are two internal sheets 31 and 32 with central holes H and two bottom sheets 33 and 34 providing the surface that contacts the body of a subject. The sheets are typically electrically conductive and provide for a distribution of electrical current. The fact that some sheets (31, 32) of electrode material are "clamped" in between top and bottom part while some sheets (33, 34) are not creates a lot of design options.

A "flat top part" 10 of an electrode interface.

A "bottom part" 20 of an electrode interface (also referred to as "eyelet").

Figure 2:
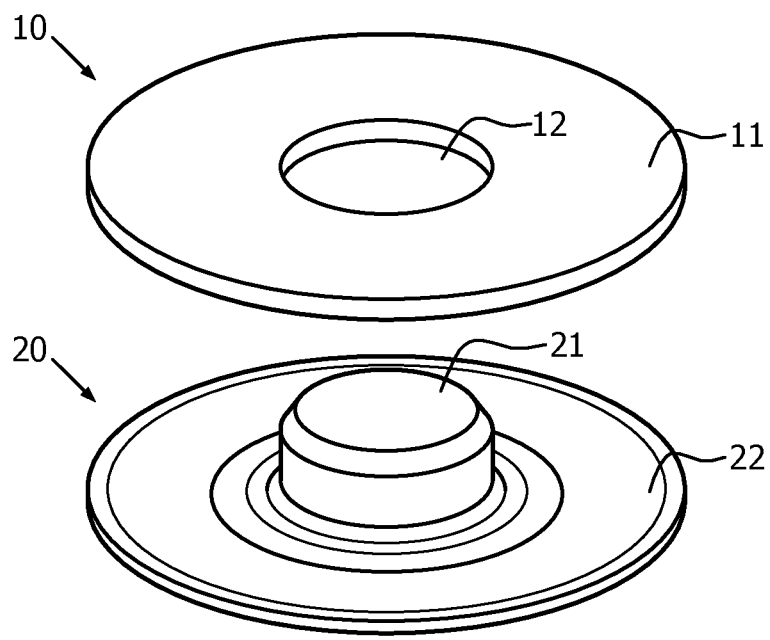
FIG. 2 shows the electrode interface of the electrode of FIG. 1 separately.

The top part 10 and the bottom part 20 (also referred to as the electrode interface) constitute means via which external equipment and/or lines of a TENS device (not shown) can electrically and mechanically be connected to the electrode 100. FIG. 2 shows the electrode interface separately in an exploded view. It can be seen that the top part 10 is designed to make good mechanical and electrical contact with the TENS device. The top part 10 is preferably a plain flat disk of e.g. 0.6 mm thickness and typically made from a metal such as from magnetic steel. In its center is a calibrated aperture 12 to enable a press fit with the bottom part 20. The edges of this aperture 12 are rounded. The purpose of the top part 10 is to provide good electrical contact to the TENS device and the bottom part and to provide magnetic force to the TENS device. Due to its simple shape of a flat disk, this part can be made very cheap and with a very reproducible flat surface 11.

The bottom part 20 has a press fit into the metal disk 10, thus making good electrical and mechanical contact to the disk. It is preferably made from a plastic such as conductive ABS. The bottom part 20 comprises a head portion 21, here a cylindrical central dome head, and a flexible flange 22. The flexible flange 22 guarantees a certain upward contact force during lifetime. The purpose of the bottom part 20 is to make good electrical contact to the electrode material (sheets 31, 32) and to provide a feature to position the electrode onto the TENS device.

Figure 3:
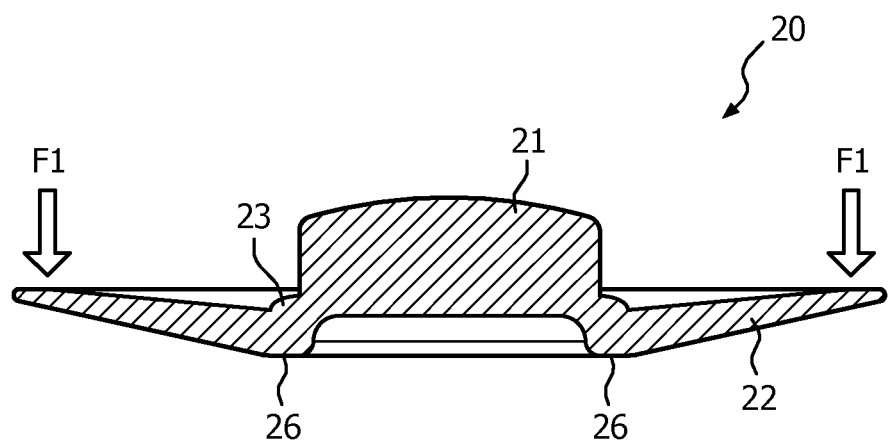
FIG. 3 shows a section through the bottom part of the electrode interface.

FIG. 3 shows a separate section through the bottom part 20. It can be seen that the head portion 21 is rounded to allow easy positioning to a TENS device. The diameter of the head portion 21 is such that it has a press fit to the aperture 12 in the disk 10. The flexible flange 22 of the eyelet 20 is flexible. When the eyelet is pressed into the aperture 12 of the disk 10, the flexible flange 22 of the eyelet 20 will be slightly deformed. Preferably, the geometry of the flexible flange 22 is designed such that it will be deformed around 0.12 mm and that the resulting contact force between the disk 10 and the eyelet 20 is in the order of 10 to 15 N. The design may preferably be based on a FEM-simulation of the eyelet. When in the course of time the press fit between eyelet and disk will have some relaxation, the flexible flange will still guarantee a contact force between about 10 and 15 N.

FIG. 3 also shows a smaller flange 23 disposed at the transition from the head portion 21 to the above described large flange 22. The purpose of this small flange 23 is to provide a stop when during assembly bottom part 20 is pressed into top part 10. This stop creates a well-defined deflexion of the large flange 22. This is further explained in detail in conjunction with FIG. 4a and FIG. 4b.

Figure 4A:
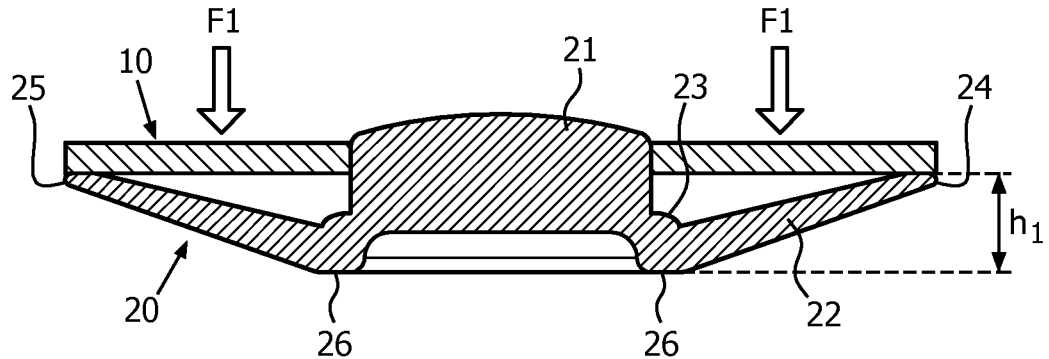
FIG. 4a and FIG. 4b show a cross sectional view of the assembly of top part and bottom part of the electrode interface.
Figure 4B:
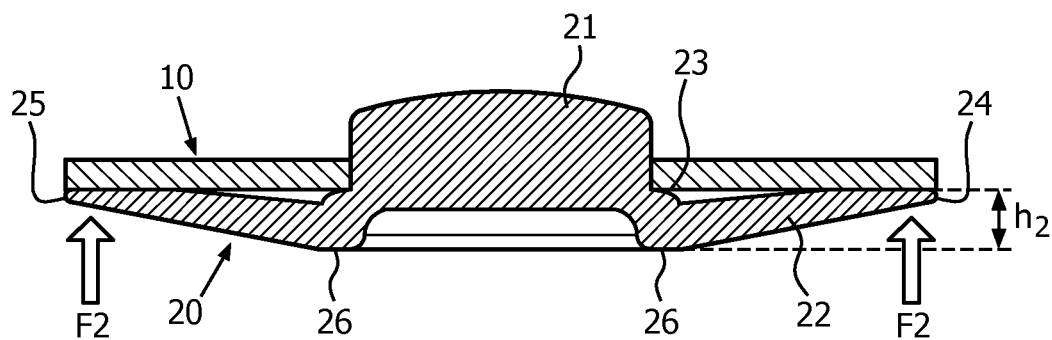

FIG. 4a and FIG. 4b shows a cross sectional view of the assembly of top part and bottom part. FIG. 4a shows an initial position, during assembly, when the flat top part 10 just touches the flexible flange 22 at corresponding distal ends, such as distal end 24 and distal end 25. At this moment, each of the distal ends 24 and 25 of the flexible flange 22 is at a first pre-determined height (h1) from the base 26 of the flexible flange 22. It may be understood that the base 26 is the lowest part of the flexible flange 22. Thereafter, the flat top part 10 is continued to be pushed downwards in the direction of the applied force F1, till the flat top part 10 encounters the flange 23. As mentioned before, the flange 23 acts as a stop. Further, as depicted in FIG. 4b, at the position where the flat top part 10 touches the flange 23, the flexible flange 22 by virtue of the force applied (F1) and nature of the material, has deflected to a second pre-determined height (h2). It is evident from the FIG. 4b, the height of the flange 23 is also the second pre-determined height (h2). In various embodiments of the invention, the first pre-determined height (h1) is greater than the second pre-determined height (h2).

Given that the material properties and the dimensions of the flexible flange 22 are known, it is thus possible to calculate a force (F2) that will be exerted by the flexible flange 22 in the upwards direction after the press fit of the top part 10 and bottom part 20 is completed. In an embodiment of the invention, the first pre-determined height (h1) and the second pre-determined height (h2) are chosen/calculated in such a way that the deflection/change/displacement in height thus created/achieved provides a desired upward force to retain the electrode sheets there between. In other words, the deflection is pre-defined and accordingly h1 and h2 can be chosen. In further embodiment of the invention, the h1 and h2 are chosen in such a way that the displacement in height thus achieved provides a desired upward force to retain the electrode sheets there between and also simultaneously supports the bio-medical device when in use.

Figure 5:
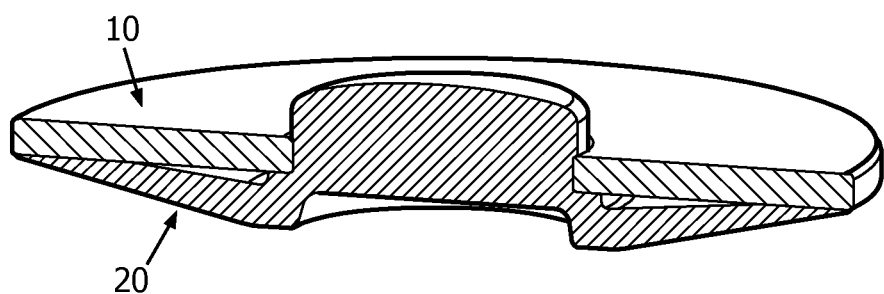

FIG. 5 shows the assembled electrode interface, i.e. the eyelet 20 being pressed into the disk 10. Electrode material clamped in between is not shown in this Figure.

In summary, an embodiment of an electrode interface and an associated electrode has been described in which the electrode interface comprises a top part with an aperture and a bottom part. The bottom part has a head portion designed for a press fit with said aperture and a flexible flange that clamps electrode sheets in the connected state of the electrode interface. The top part may preferably have the shape of a disk of magnetic or magnetizable material. The bottom part may preferably be made from a conductive plastic such as ABS. The electrode interface may particularly be used in a TENS device. The design is such that the contact force remains unchanged over time or at least the remaining contact force is still large enough.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A bio-medical electrode comprising:
   a) a flat top part having an aperture;
   b) a bottom part having:
      a flexible flange having an upward inclination;
      an upward projecting head portion that can be fixed in the aperture, wherein the upward projecting head portion comprises a central dome head disposed on the flexible flange;
      a stop flange disposed on the flexible flange at a transition between the upward projecting head portion and the flexible flange; and
   c) an electrode material;
   wherein the stop flange is arranged to provide (i) a mechanical stop and (ii) a displacement in height for creating a pre-defined deflection of the flexible flange to provide a desired upward contact force when the flat top part along with the electrode material is pressed against the flexible flange and stopped via the stop flange, with the upward projecting head portion fixed in the aperture of the flat top part.

2. The electrode according to claim 1, wherein each of distal ends of the upward inclination of the flexible flange is at a first pre-determined height from a base of the flexible flange, wherein the stop flange is at a second pre-determined height from the base of the flexible flange, and wherein the first pre-determined height is greater than the second pre-determined height.

3. The electrode according to claim 2, wherein the pre-defined deflection is created by displacement of each of the distal ends of the flexible flange from the first pre-determined height to the second pre-determined height.

4. The electrode according to claim 1, wherein the flat top part is comprised of magnetic or magnetizable material for connecting with a bio-medical device.

5. The electrode according to claim 1, wherein the re-defined deflection of the flexible flange provides the desired upward contact force for retaining the electrode material between the top flat part and the bottom part, the desired upward contact force ranging between about 5 N and about 20 N.

6. The electrode according to claim 1, wherein the flexible flange is cone-shaped.

7. The electrode according to claim 1, wherein the bottom part is electrically conductive.

8. The electrode according to claim 1, wherein the flat top part is electrically conductive.

9. The electrode according to claim 1, wherein the head portion of the bottom part is fixed in the aperture of the flat top part by a press fit or a snap connection.

10. The electrode according to claim 1, wherein one or more of the aperture and the upward projecting head portion has edges that are rounded.

11. The electrode according to claim 1, wherein the flat top part and the bottom part together comprise an electrode interface for at least one selected from the group consisting of a TENS electrode, a ECG electrode, a EEG electrode, an electromyography electrode, an electrical muscle stimulation electrode, a neuromuscular stimulation electrode, and a functional electrical stimulation electrode.

12. The electrode according to claim 1, wherein the electrode material comprises one or more electrode sheets.

13. The electrode according to claim 12, wherein each of the one or more electrode sheets has a hole through which the upward projecting head portion of the bottom part extends.

* * * * *